United States Patent [19]
Nishina et al.

[11] Patent Number: 6,125,332
[45] Date of Patent: Sep. 26, 2000

[54] METHOD AND DEVICE FOR DISPLAYING A COMPOUND STRUCTURE

[75] Inventors: Shinichi Nishina, Fukuoka; Seiichi Aikawa; Fumiko Matsuzawa, both of Kawasaki, all of Japan

[73] Assignee: Fujitsu Limited, Kawasaki, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/620,289

[22] Filed: Mar. 22, 1996

[30] Foreign Application Priority Data

Mar. 31, 1995 [JP] Japan ................. 7-076765

[51] Int. Cl.$^7$ .......................................... G06F 17/00
[52] U.S. Cl. .......................... 702/32; 395/500.33
[58] Field of Search ................... 364/496, 497, 364/498, 499, 578, 550; 395/133, 770, 118, 119, 131, 167, 500.33; 702/27, 32; 711/101; 707/526, 528, 529; 345/302, 115, 116, 340, 507

[56] References Cited

U.S. PATENT DOCUMENTS

| | | | |
|---|---|---|---|
| 4,747,059 | 5/1988 | Hirayama et al. | 364/496 |
| 5,321,804 | 6/1994 | Kusaba et al. | 395/770 |
| 5,337,402 | 8/1994 | Kitagawa et al. | 395/133 |
| 5,704,051 | 12/1997 | Lane et al. | 345/357 |
| 5,708,764 | 1/1998 | Borrel et al. | 395/119 |
| 5,710,878 | 1/1998 | McCoy et al. | 395/129 |

FOREIGN PATENT DOCUMENTS 6-180737  6/1994  Japan .

OTHER PUBLICATIONS

Smith, "MolView: A Program to Analyze and Display Atomic Structures" SciTech Journal Jan., 1995 p. 24–25.
HyperChem for Windows. Reference Manual. Jul. 21, 1993 p. 4, 65–67, 77–82, 98–104, 126–127, 130–131, 135, 148–149, 153–154, 162–167, 228–231.
Introduction to Protein Structure, Branden and Tooze, Garland Publishing, Inc., 1991, pp. 3–4, 6–7 and 121.

Primary Examiner—M. Kemper
Attorney, Agent, or Firm—Staas & Halsey LLP

[57] ABSTRACT

A method and a device for displaying a structure of a compound provide a graphic display and a related character display, affording improved operational characteristics. Stereo structural data obtained from a database is stored in a display buffer provided with a designated area for setting a display mode, thereby displaying graphically a stereo structure of said compound corresponding to the display mode set in said designated area and displaying characters representing said structure of said compound corresponding to said display mode set in said designated area.

18 Claims, 14 Drawing Sheets

FIG. 2

| | 40 | 41 | 42 | 43 | 44 | 45 | 46 | 47 | 48 | 49 | 49a |
|---|---|---|---|---|---|---|---|---|---|---|---|
| ATOM | 90 | N | LYS | 13 | 7.099 | 16.941 | -0.037 | 1.00 | 33.91 | 2LZ2 | 170 |
| ATOM | 91 | CA | LYS | 13 | 8.214 | 16.744 | 0.837 | 1.00 | 28.68 | 2LZ2 | 171 |
| ATOM | 92 | C | LYS | 13 | 9.440 | 16.568 | -0.144 | 1.00 | 56.73 | 2LZ2 | 172 |
| ATOM | 93 | O | LYS | 13 | 10.582 | 17.098 | 0.038 | 1.00 | 67.85 | 2LZ2 | 173 |
| ATOM | 94 | CB | LYS | 13 | 8.212 | 15.592 | 1.809 | 1.00 | 25.00 | 2LZ2 | 174 |
| ATOM | 95 | CG | LYS | 13 | 9.446 | 15.752 | 2.747 | 1.00 | 42.53 | 2LZ2 | 175 |
| ATOM | 96 | CD | LYS | 13 | 9.533 | 14.886 | 3.985 | 1.00 | 49.06 | 2LZ2 | 176 |
| ATOM | 97 | CE | LYS | 13 | 10.955 | 14.527 | 4.383 | 1.00 | 55.81 | 2LZ2 | 177 |
| ATOM | 98 | NZ | LYS | 13 | 11.460 | 13.244 | 3.720 | 1.00 | 63.67 | 2LZ2 | 178 |
| ATOM | 99 | N | ARG | 14 | 9.153 | 15.855 | -1.199 | 1.00 | 48.62 | 2LZ2 | 179 |
| ATOM | 100 | CA | ARG | 14 | 10.108 | 15.521 | -2.322 | 1.00 | 54.11 | 2LZ2 | 180 |
| ATOM | 101 | C | ARG | 14 | 10.230 | 16.779 | -3.193 | 1.00 | 54.00 | 2LZ2 | 181 |
| ATOM | 102 | O | ARG | 14 | 11.373 | 17.271 | -3.462 | 1.00 | 56.53 | 2LZ2 | 182 |
| ATOM | 103 | CB | ARG | 14 | 9.655 | 14.150 | -2.757 | 1.00 | 41.97 | 2LZ2 | 183 |
| ATOM | 104 | CG | ARG | 14 | 9.618 | 13.526 | -4.089 | 1.00 | 49.55 | 2LZ2 | 184 |
| ATOM | 105 | CD | ARG | 14 | 9.224 | 12.192 | -4.458 | 1.00 | 30.12 | 2LZ2 | 185 |
| ATOM | 106 | NE | ARG | 14 | 7.851 | 11.953 | -5.016 | 1.00 | 39.81 | 2LZ2 | 186 |
| ATOM | 107 | CZ | ARG | 14 | 7.086 | 12.794 | -5.672 | 1.00 | 34.83 | 2LZ2 | 187 |
| ATOM | 108 | NH1 | ARG | 14 | 7.426 | 14.052 | -5.971 | 1.00 | 32.38 | 2LZ2 | 188 |
| ATOM | 109 | NH2 | ARG | 14 | 5.856 | 12.420 | -6.072 | 1.00 | 36.72 | 2LZ2 | 189 |
| ATOM | 110 | N | LEU | 15 | 9.079 | 17.411 | -3.453 | 1.00 | 40.14 | 2LZ2 | 190 |
| ATOM | 111 | CA | LEU | 15 | 8.816 | 18.622 | -4.219 | 1.00 | 29.70 | 2LZ2 | 191 |
| ATOM | 112 | C | LEU | 15 | 9.447 | 19.843 | -3.596 | 1.00 | 50.24 | 2LZ2 | 192 |
| ATOM | 113 | O | LEU | 15 | 9.665 | 20.921 | -4.223 | 1.00 | 44.07 | 2LZ2 | 193 |
| ATOM | 114 | CB | LEU | 15 | 7.304 | 18.588 | -4.641 | 1.00 | 13.97 | 2LZ2 | 194 |
| ATOM | 115 | CG | LEU | 15 | 7.127 | 18.861 | -6.144 | 1.00 | 8.99 | 2LZ2 | 195 |
| ATOM | 116 | CD1 | LEU | 15 | 7.986 | 20.171 | -6.378 | 1.00 | 4.30 | 2LZ2 | 196 |
| ATOM | 117 | CD2 | LEU | 15 | 8.173 | 18.180 | -7.104 | 1.00 | 14.15 | 2LZ2 | 197 |
| ATOM | 118 | N | GLY | 16 | 9.830 | 19.702 | -2.331 | 1.00 | 52.43 | 2LZ2 | 198 |
| ATOM | 119 | CA | GLY | 16 | 10.460 | 20.564 | -1.358 | 1.00 | 27.40 | 2LZ2 | 199 |
| ATOM | 120 | C | GLY | 16 | 9.622 | 21.351 | -0.422 | 1.00 | 32.36 | 2LZ2 | 200 |
| ATOM | 121 | O | GLY | 16 | 10.274 | 22.177 | 0.205 | 1.00 | 53.59 | 2LZ2 | 201 |

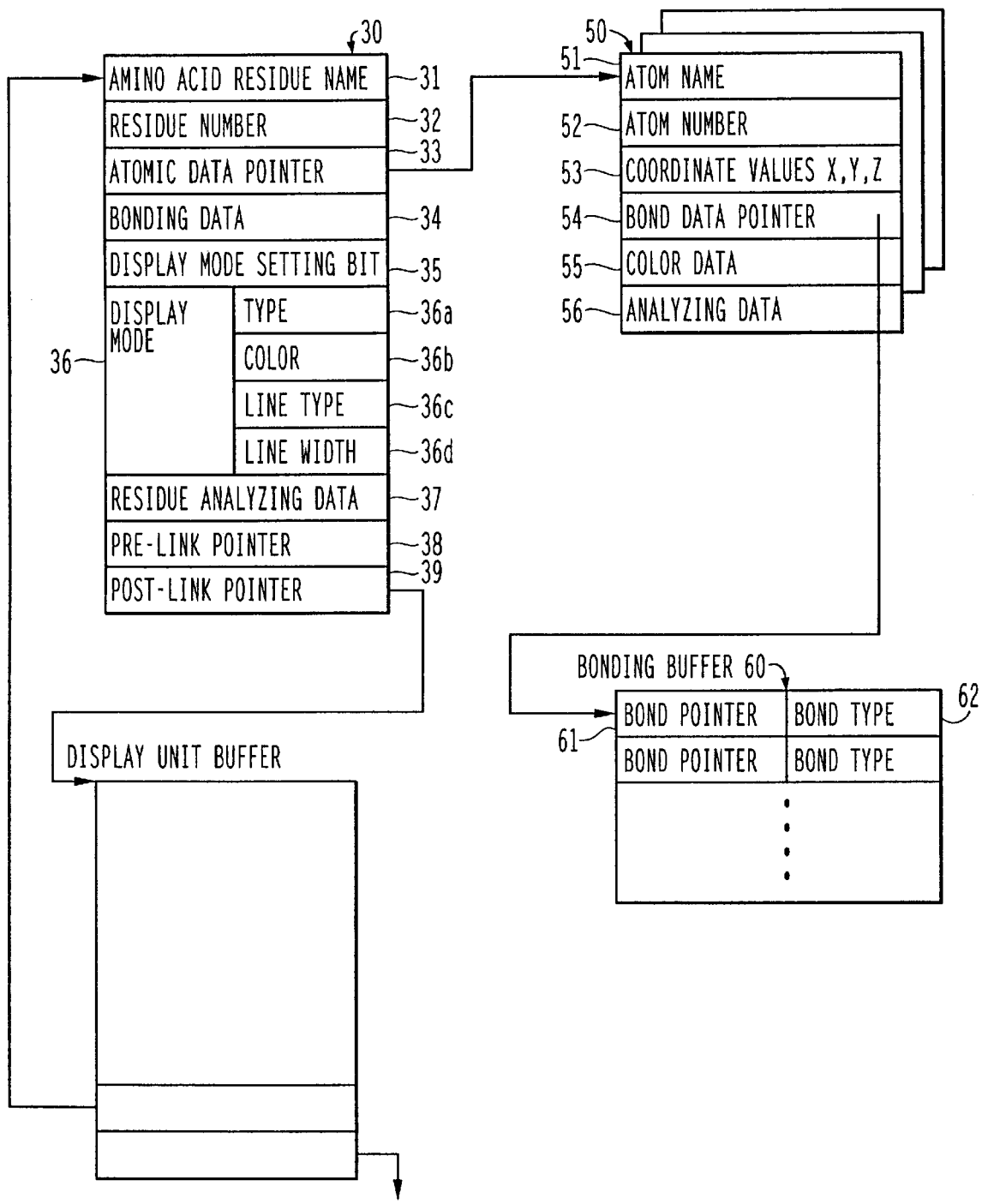

METHOD AND DEVICE FOR DISPLAYING A COMPOUND STRUCTURE

BACKGROUND OF THE INVENTION

1. Field of the Invention

The present invention generally relates to a method and a device for displaying a three-dimensional structure of a protein, and more particularly to a method for displaying a three-dimensional structure of a protein in which the three-dimensional structure of the protein is displayed in a graphic display or a character display.

2. Description of the Related Art

In the field of chemistry or physics, three-dimensional structures of various compounds are determined by using an X-ray diffraction crystal structure analysis or an NMR. The obtained data is stored in a database in order to support an analysis of the compound and production of a new compound. Protein Data Bank (PDB) is one of the most famous databases in which the stereo structures of the proteins obtained by the X-ray diffraction crystal structure analysis are stored. Also, Cambridge Structural Database (CSD) is widely known in which chemical compounds are registered.

The protein is a biopolymer in which a plurality of amino acids are bonded in a single chain in a primary structure. When the chain is folded to form a higher-order structure, various functions are revealed. Each amino acid of the protein is identified by a number resulting from numbering from an N-terminus to a C-terminus. The number is called an amino acid sequence number or an amino acid residue number. Each amino acid includes a plurality of atoms. Therefore, in the above PDB, a name of the protein, an identification number of the protein, amino acid numbers constituting the protein, atoms constituting the amino acids and a third-order coordinate of the atoms constituting the amino acids are included.

According to research, it has been found that the stereo structure (three-dimensional structure) of the compound is strongly related to the function thereof. In order to produce a new compound having a new function, a relationship between the stereo structure and the function has been studied through chemical experimentation. Between compounds having the same functions, a common specific structure is considered to influence the function of the compound. Thus, for the purpose described above, the screening of the compound having the specific structure is indispensable.

Japanese Laid-Open Patent Application 6-180737 discloses a device for displaying a stereo structure of a protein having a database in which stereo structure data of proteins are recorded. In this device, each amino acid constituting the protein is handled as a group of elements having a certain sequence, according to the database. When each group is related, a screening is performed based on a geometric relationship, a predetermined threshold or a function of the amino acid to find combinations satisfying the above requirement. Among the combinations, an amino acid sequence in which an average distance between each element is a minimum is found. After that, a position and a direction is determined so as to overlap the stereo structures of the protein.

In the preparation step of the overlapping of the stereo structure of the protein, a stereographic display of the protein structure data read from the database is conducted. Also, a character display of the protein structure data, in which each amino acid constituting the protein is represented by a character and the protein is displayed as a character line, is performed.

However, in the conventional method described above, the graphic display is not related to the character display. For example, when a certain range of amino acids is specified in the graphic display of the protein, the specified range of the amino acids is not defined in the character display. Thus, operational characteristics of the device are not adequate, especially for unskilled operators.

SUMMARY OF THE INVENTION

Accordingly, it is a general object of the present invention to provide a novel and useful method and device for displaying a structure of a compound in which a graphic display is related to the character display to improve operational characteristics.

The above object of the present invention is achieved by a method for displaying a structure of a compound with reference to a database in which stereo structural data of the compound is stored, comprising the steps of recording the stereo structural data obtained from the database in a display buffer provided with a designated area for setting a display mode, displaying graphically a stereo structure of the compound corresponding to the display mode set in the designated area, and displaying characters representing the structure of the compound corresponding to the display mode set in the designated area.

The above object of the present invention is also achieved by a device for displaying a structure of a compound comprising a database in which stereo structural data of the compound is stored, a display buffer in which the stereo structural data of the database is recorded, the display buffer being provided with a designated area for setting a display mode, and a display unit for displaying the structure of the compound, wherein a stereographic structure of the compound and characters representing the structure of the compound are displayed in the display unit, corresponding to the display mode set in the designated area.

According to the invention, the graphic display of the compound can be related to the character display.

In the above invention, the compound may be a protein and the display buffer may be a group of display unit buffers for each amino acid residue unit of the protein. According to the invention, the graphic display of the protein can be related to the character display.

In the above invention, the display mode may be determined by setting a shape, a color, a line width or a line type defining the stereo structure of the compound and the display mode may also be determined by setting a font, a highlight or a color of the characters representing the structure of the compound.

According to the invention, the graphic display of the compound can be related to the character display in that the font, the highlight or the color in the character display can be changed in response to a change in the shape, the color, the line width and the line type in the graphic display.

In the above invention, the compound may be a nucleic acid and the display buffer may be a group of display unit buffers for each base unit of the nucleic acid. According to the invention, the graphic display of the nucleic acid can be related to the character display.

In the above invention, the compound may be a hetero atomic compound and the display buffer may be a group of display unit buffers for each hetero atom unit of the hetero atomic compound. According to the invention, the graphic display of the hetero atomic compound can be related to the character display.

Other objects and further features of the present invention will be apparent from the following detailed description when read in conjunction with the accompanying drawings.

BRIEF DESCRIPTION OF THE DRAWINGS

FIG. 2 is a schematic illustration showing a PDB;

FIG. 3 is a schematic illustration showing a display buffer;

DESCRIPTION OF THE PREFERRED EMBODIMENTS

The preferred embodiments of the present invention will now be described in further detail with reference to the accompanying drawings.

Figure 1:
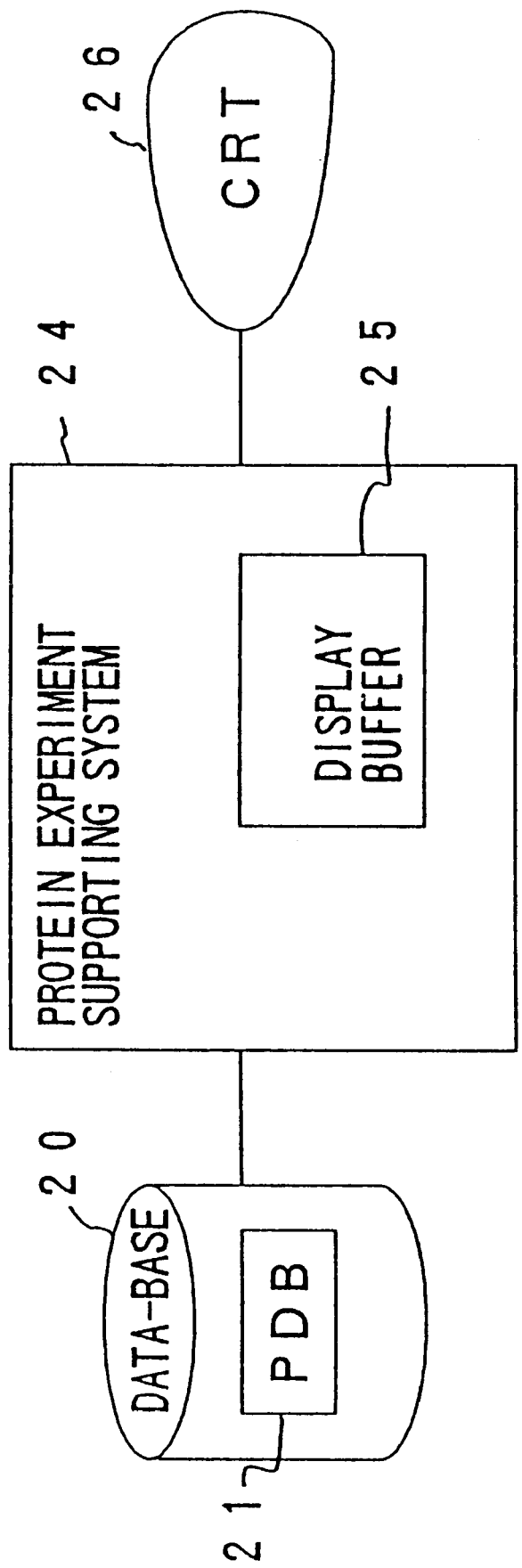
FIG. 1 is a basic block diagram showing a device for displaying a compound structure of the present invention.

FIG. 1 is a schematic illustration showing a system of the present invention. In FIG. 1, a PDB 21 is installed in a database 20. A protein experiment supporting system 24 accesses the PDB 21 to read stereo structural data of a desired protein. That data is sent to a display buffer 25 in the protein experiment supporting system 24. The data is sent from the display buffer 25 to a CRT 26 to perform a graphic display and a character display of the protein.

In the PDB 21, the stereo-chemical structure of the protein is recorded, whereby an atom of the protein is displayed in each line, as shown in FIG. 2. The database 20 includes various data such as an atomic number 40, an element abbreviation 41, an amino acid residue name 42, an amino acid residue number 43, X-coordinate 44, Y-coordinate 45, Z-coordinate 46, an existence probability 47, a temperature factor 48, a protein ID 49 and a record number 49*a* of the atom in the protein, each of which is displayed in each line.

FIG. 3 shows a display buffer memory 25, in which a plurality of display buffer memories for each unit of the amino acid residue are linked. The display unit buffer 30 includes an amino acid residue name 31, an amino acid residue number 32, an atomic data pointer 33, bonding data 34 to the other amino acid residue, a display mode setting bit 35, a display mode value 36, amino acid residue analyzing data 37, a pre-link pointer 38 and a post link pointer 39.

The atomic data pointer 33 points to the starting address of a selected one of the atomic buffer 50 storing data of the atoms constituting an amino acid residue. The bonding data 34, to the other amino acid residue, points to the other amino acid residue bonded to the amino acid residue. The display mode setting bit 35 is four bits, which display whether or not a display mode factor, such as a type of display, a color, a type of the line, or a width of line, is set. The display mode value 36 includes a type 36*a*, a color 36*b*, line type 36*c* and a line width 36*d*.

Thus, the protein experiment supporting system 24 reads stereo data of the structure shown in FIG. 2, from the PDB 21 to form the display unit buffer 30 for each amino acid residue. The display data is stored in the display buffer 25. The display mode setting bit 35 and the display mode value 36 in the display unit buffer 30 in the display buffer 25 can be set by the display unit buffer 30. In the residue analyzing data 37, analyzing data of the amino acid is set. In the pre-link pointer 38, the starting address of a previous display unit buffer 30, which is linked to the present one, is recorded. In the post-link pointer 39, a starting address of a following display unit buffer 30, which is linked the present one, is recorded The number of the atomic buffers 50 linked by the atomic data pointer 33 is equal to the number of the atoms of the amino acid residue. Each atomic buffer 50 includes the name of the atom 51, an atomic number 52, coordinate values 53 (X-axis, Y-axis, Z-axis), a bonding data pointer 54, color data 55 and analyzing data 56 for each atom. The bonding data pointer 54 points to the starting address of the bonding buffer 60 storing a pair of the bond pointers 61 of a bonded atom and a type of bond 62, such as a single bond or double bond. In the color data 55, color for each atom is included. In the analyzing data 56, a temperature factor of the atom is set.

Figure 4:
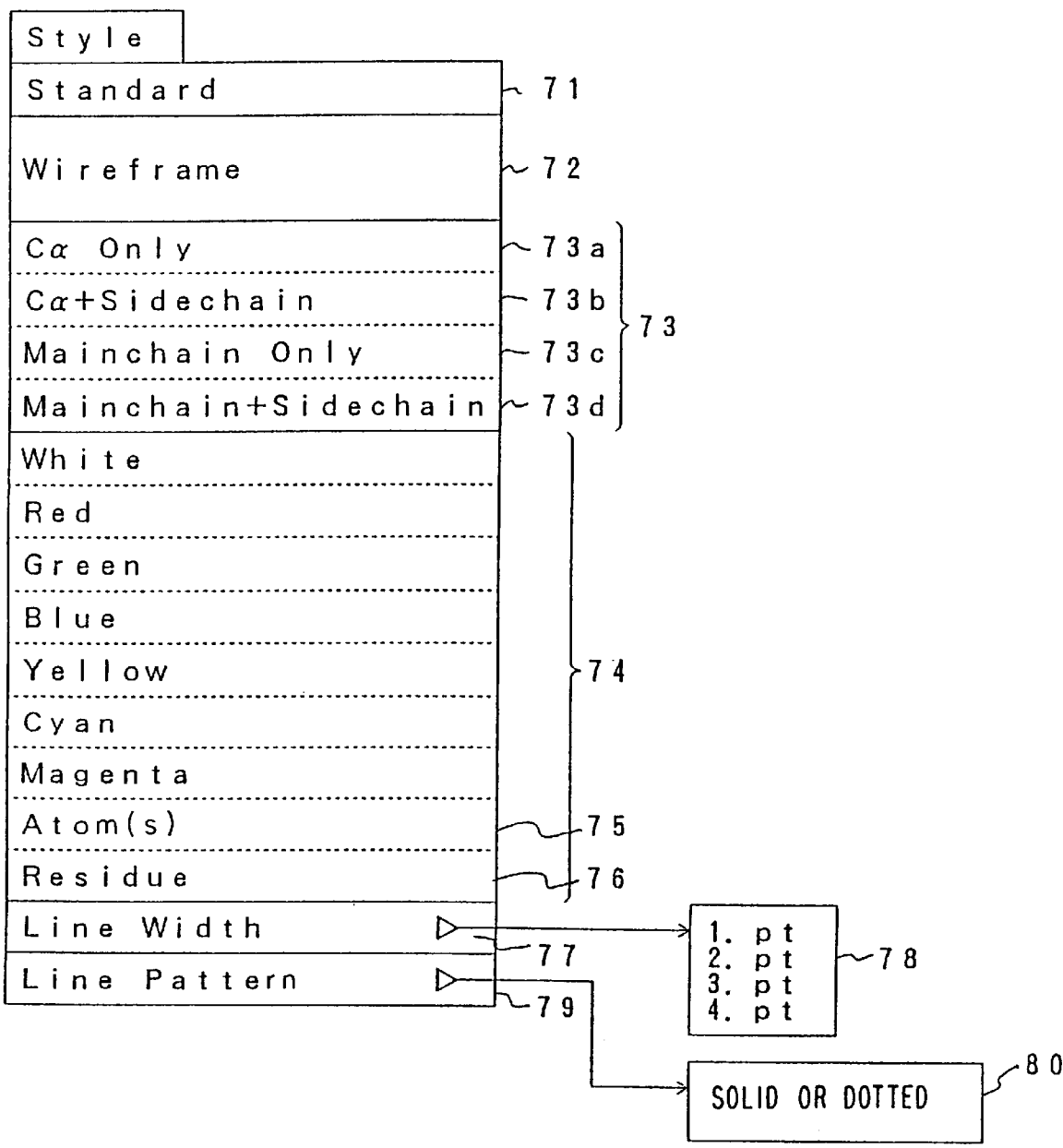
FIG. 4 is a schematic illustration showing a mode change menu.
Figure 5:
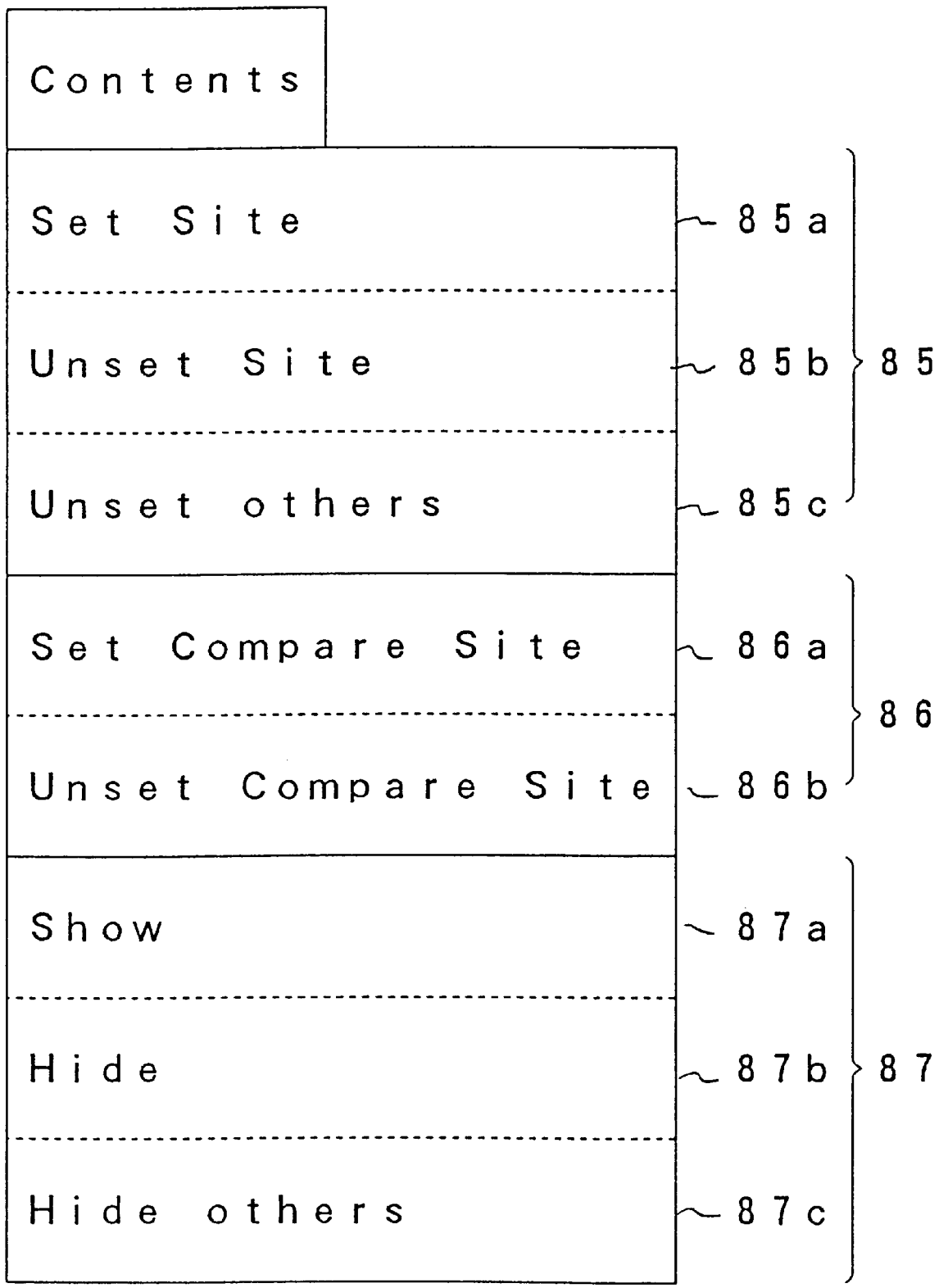
FIG. 5 is a schematic illustration showing a mode change menu.

FIGS. 4 and 5 show a display mode changing menu in the protein experiment supporting system 24. The display mode includes a style, which is a mode of drawing, and contents which are attributes or conditions for analyzing. FIG. 4 shows a style changing menu and FIG. 5 shows a contents changing menu.

In FIG. 4, when a row 71 is selected, a display attribute set previously is released and standard display of the designated amino acid residue is directed. When a row 72 is selected, a display model of a wire frame of the designated amino acid residue is ordered.

A column 73 directs the display type of the designated amino acid residue. When a row 73*a* is selected, a carbon atom Cα bonding to a side chain of the amino acid residue is displayed. When a row 73*b* is selected, the carbon atom Cα and the side chain bonding thereto are displayed. When a row 73*c* is selected, a main chain of the amino acid residue is displayed, and when a row 73*d* is selected, the main chain and the side chain, that is, a whole amino acid residue is displayed. A column 74 designates the color of the displayed amino acid residue. When a row 75 in the column 74 is selected, atoms constituting the amino acid residue are displayed in a manner such that, for example, carbon atoms are displayed in red and oxygen atoms are displayed in yellow. When a row 76 in the column 74 is selected, each amino acid residue is colored in a manner such that, for example, aniline is green and glycine is blue.

When a row 77 is selected, a column 78 is displayed. A line width in the display can be set selectively to from 1 to 4 points. When a row 79 is selected, a column 80 is displayed. In this case, the displayed line can be selected as either a solid line or a dotted line.

In FIG. 5, a column 85 sets a cutoff area. When a row 85a is selected, cutting off of a designated area is directed. When a row 85b is selected, the designation of the area is released. When a row 85c is selected, the designation of other areas is released.

A column 86 sets an area for comparison. When a row 86a is selected, a designated area is set to be a comparison object. When a row 86b is selected, the designated area is released from being a comparison area. In this context, the comparison means a comparison overlapping stereo structures of the proteins, as disclosed in the Japanese Laid-Open Patent Application No. 6-180737.

A column 87 sets a display of a designated range to visible or invisible. When a row 87a is selected, a visible display of the designated range is ordered. When a row 87b is selected, an invisible display of the designated range is ordered. When a row 87c is selected, an invisible display of the undesignated range is ordered.

In the protein experiment supporting system 24, a stereo structure of a protein or an amino acid is displayed on a graphic display. Also, the amino acid residues are displayed in a character display using abbreviations.

In this case, for example, alanine (Ala) is represented by A, arginine (Arg) is represented by R, lysine (Lys) is represented by K, leucine (Leu) is represented by L, glycine (Gly) is represented by G, asparagine (Asn) is represented by N, and cysteine (CYS) is represented by C.

The graphic display and the character display have different windows. However, they can be displayed in a multi-window display relating the graphic display to the character display. When the standard mode is selected in the row 71 shown in FIG. 4, the characters are displayed in the courier font in the character display. When the column 71 is not selected, the graphic display is conducted as directed in the row 72 and the column 73, and characters are displayed in boldface type in the character display.

When a certain color is designated in the column 74, the designated color is displayed in both the graphic display and the character display. In this case, the character display may be made in monochrome.

When one of the rows 87a–87c is selected, the designated area is displayed one dot thicker then the other part. In the character display, the character is displayed in italics. When the cutting off is designated in one of the rows 85a–85c, the line is displayed one dot thicker than the other part in the graphic display, and the designated area is displayed as an outline, in which only a border of the character is displayed in the character display. When a comparison is designated in one of the rows 86a, 86b, the designated area is displayed one dot thicker in the graphic display, and the designated area is underlined in the character display.

When an area is designated by dragging of a mouse, the designated area is one point than the other area in the graphic display, and the color of the characters in the designated area is reversed in the character display.

Figure 6:
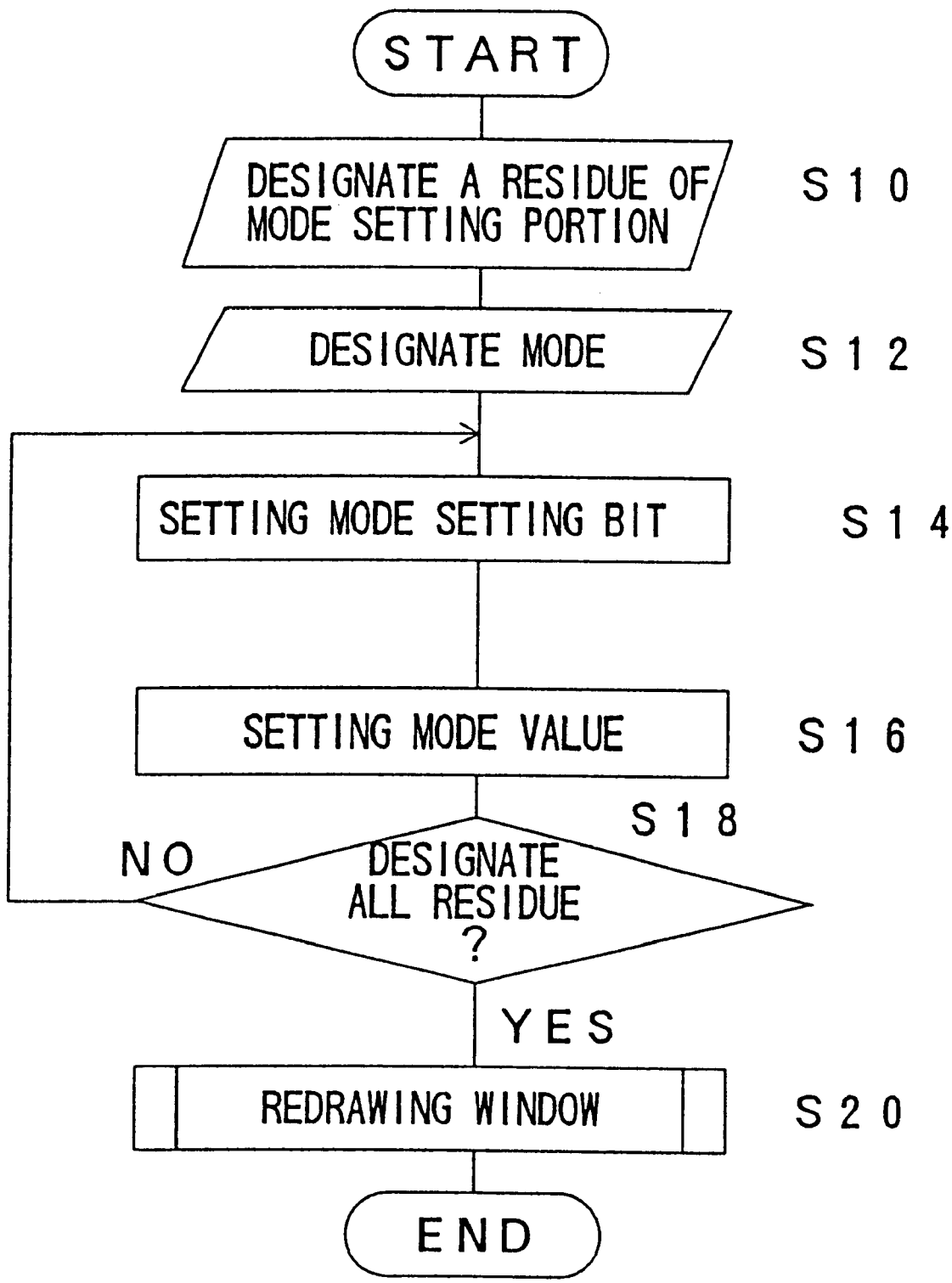
FIG. 6 is a flowchart showing a display processing.

FIG. 6 is a flow chart showing a process performed by the protein experiment supporting system 24. Referring to FIG. 6, an amino acid residue to be changed, in a display mode in the protein shown in the graphic display window or the character display window is designated in a step S10. In this case, one or a plurality of the amino acid residues may be designated. In step S12, the display mode is designated in the menu shown in FIG. 4 or FIG. 5.

In step S14, according to the designation of the display mode, the display mode setting bit 35 in the designated amino acid residue display unit buffer 30 is set. Also, in step S16, the display mode value 36 in the display unit buffer 30 is set, according to the designation of the display mode.

The above steps S14, S16 are performed in all display unit buffers 30 of the designated amino acid residues. When all display unit buffers 30 are defined in step 18, the display window is redrawn in step S20.

Figure 7:
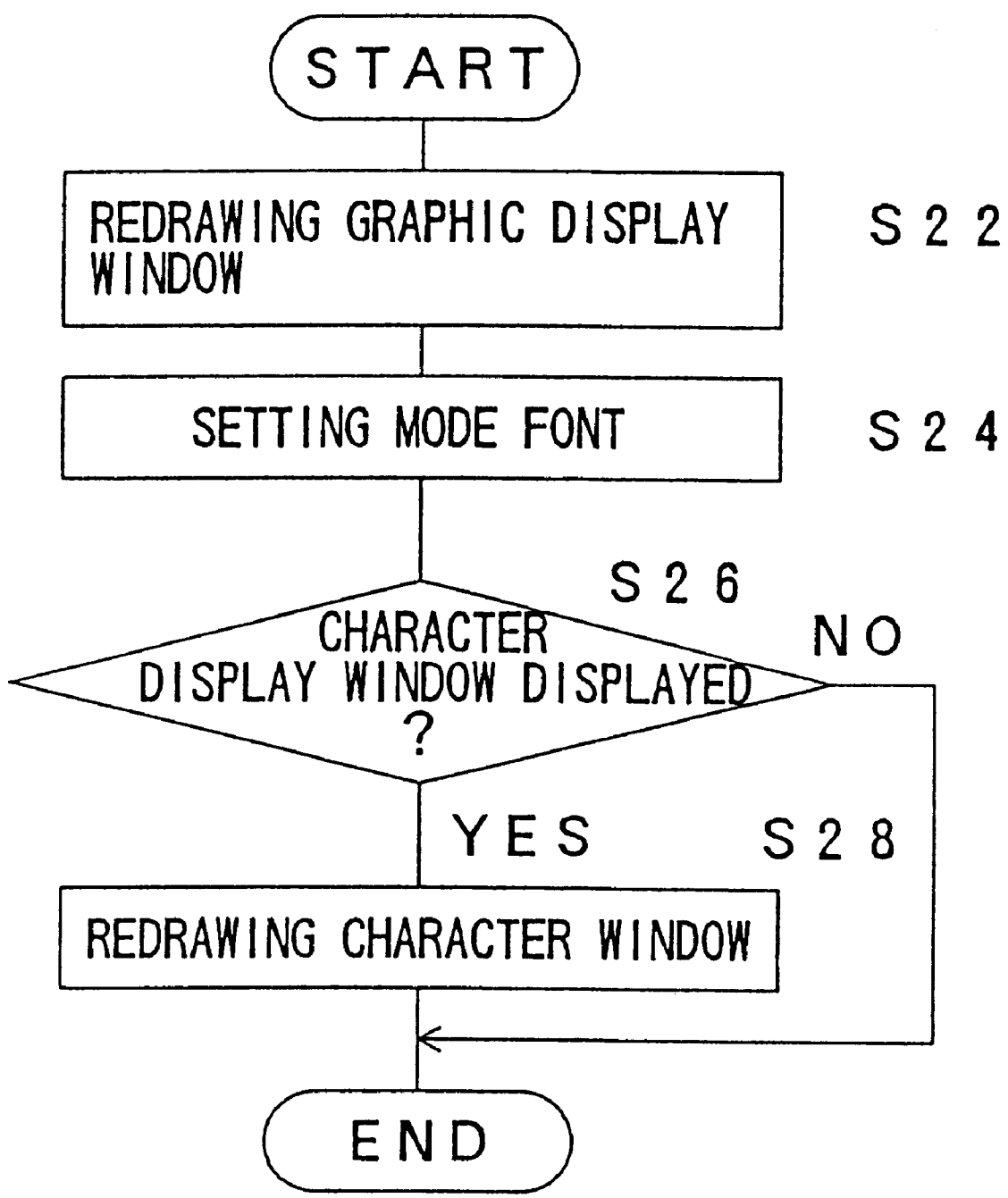
FIG. 7 is another flowchart showing the display processing.

FIG. 7 is a flow chart showing a redrawing of the display window in the step S20. In FIG. 7, the protein stereo structure shown in the graphic display window is redrawn by using a display unit buffer 30 in which a display mode is changed, in a step S22. Next, a font for the character display is set by using a display unit buffer 30 in which the display mode is changed, in a step S24.

In step S26, it is determined whether or not the character display window is displayed. When the character display window is not displayed, the process is ended. When the character display window is displayed, the character display window is displayed, using a font set in the step 24, in step S28 to end the process.

Figure 8:
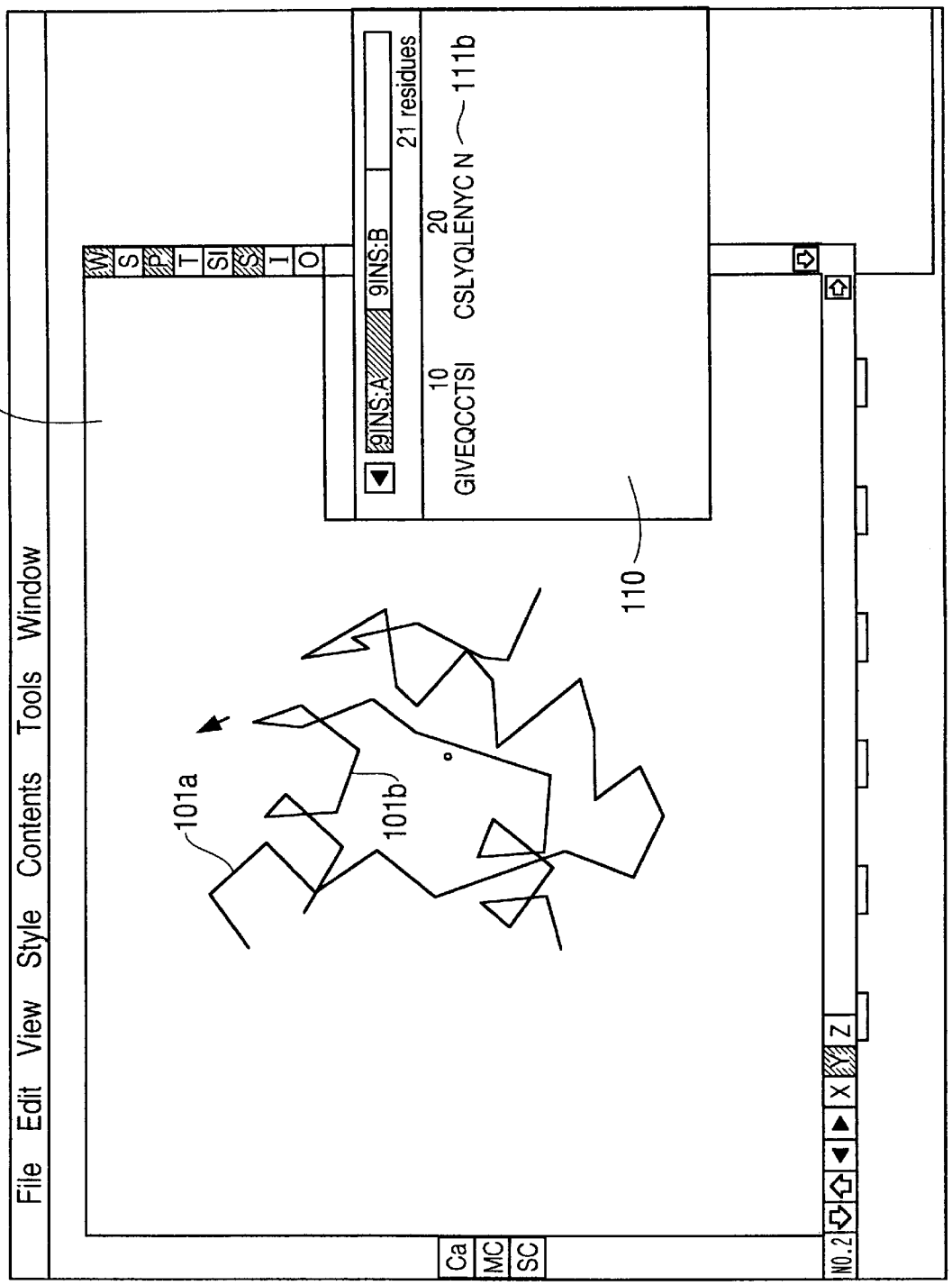
FIG. 8 is a schematic illustration showing an example of a display in the present invention.

Next, examples of the display in the present invention will be described, referring to the drawings. FIG. 8 shows a standard display, which is displayed when the row 71 is selected in the menu shown in FIG. 4. In the graphic display window 100, stereo structures 101a, 101b are displayed. In the character display window 110, the character display 111b of the protein, which corresponds to the stereo construction 101b, is displayed. In the character display, only the courier font is used.

Figure 9:
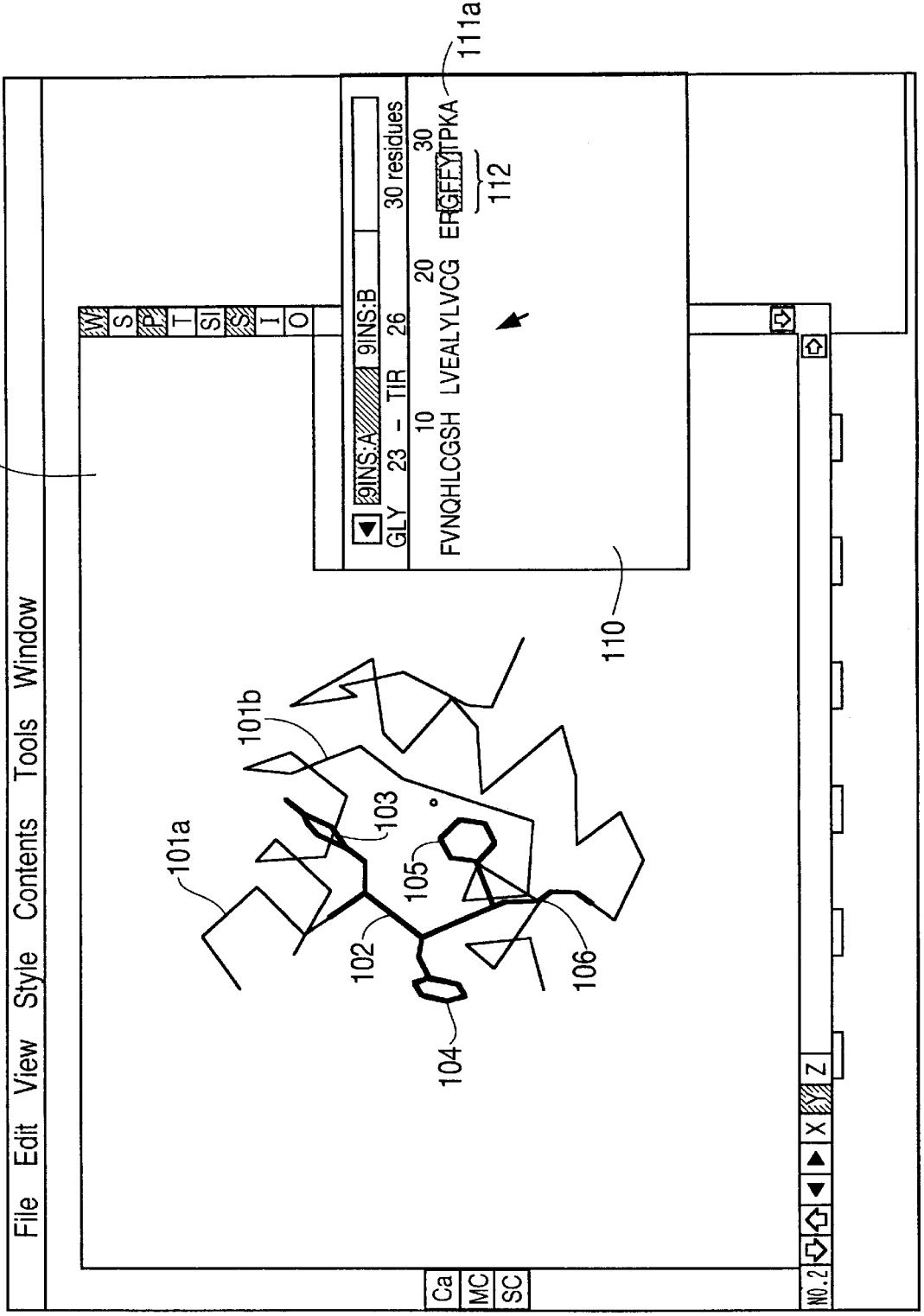
FIG. 9 is a schematic illustration showing another example of the display in the present invention.

FIG. 9 shows a graphic display window 100 showing a side-chain of a carbon atom Cα when a portion 102 of the stereo display 101a of the protein in the graphic window is designated and the row 73b is selected in the display mode menu. The portion 102 is displayed one point wider than the other part, or portion, and the side chains 103–106 are displayed.

Also, in the character display 111a of the protein in the character display window 110, which corresponds to the portion 101a, the color of the portion 112 corresponding to the portion 102 is reversed using a boldface type.

Figure 10:
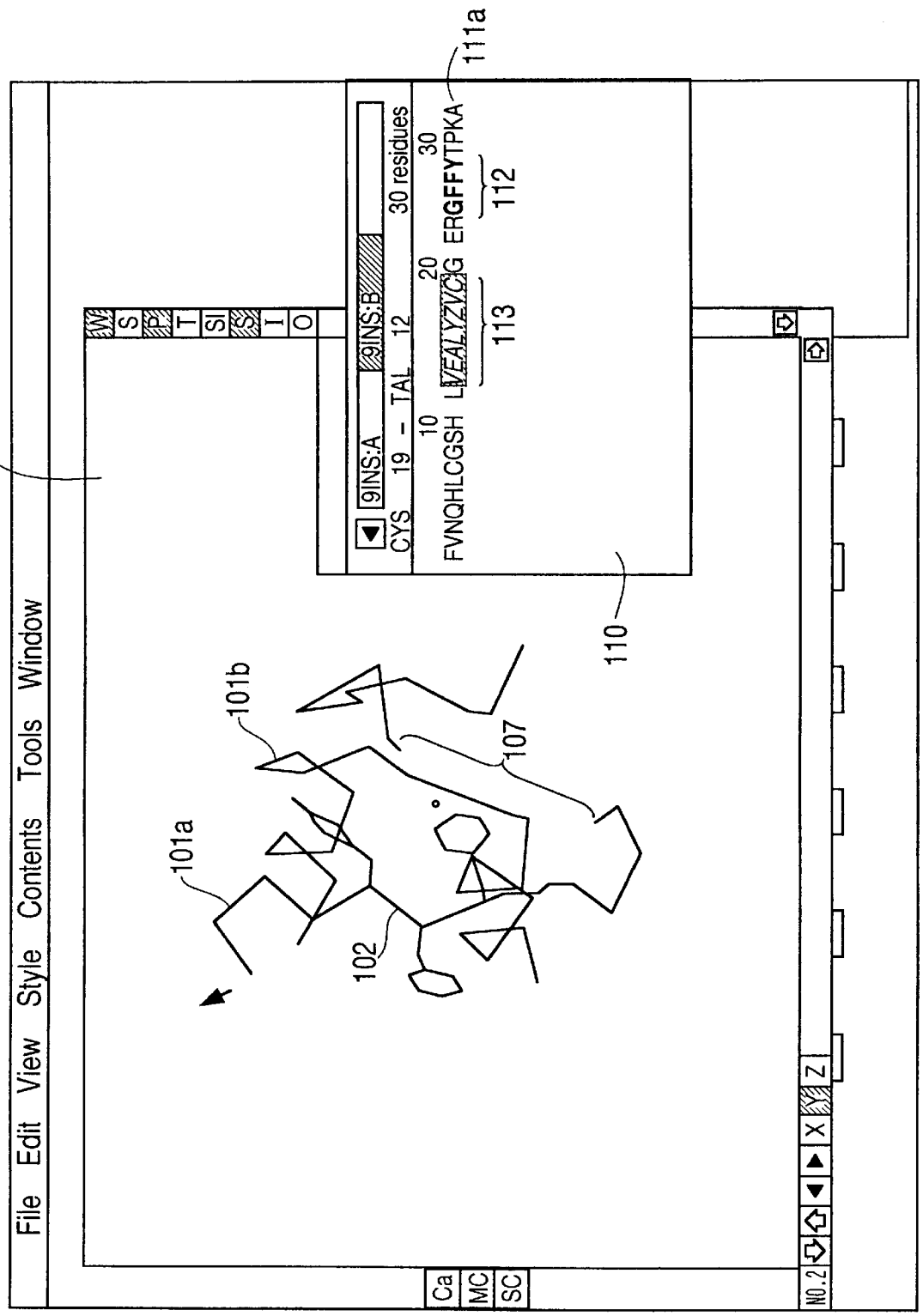
FIG. 10 is a schematic illustration showing another example of the display in the present invention.

In FIG. 10, a portion 107, in the three dimensional stereo display 101a of the protein in the graphic display window 100 shown in FIG. 9, is designated and the row 87b is selected in the display mode changing menu, to make the portion 107 invisible. In this case, the designated portion 107 is not displayed.

In the character display of the protein in the character display window 110, a portion 112 is displayed in the bold face type and the portion 113, which corresponds to the portion 107, is displayed in italics with the color in reverse.

Figure 11:
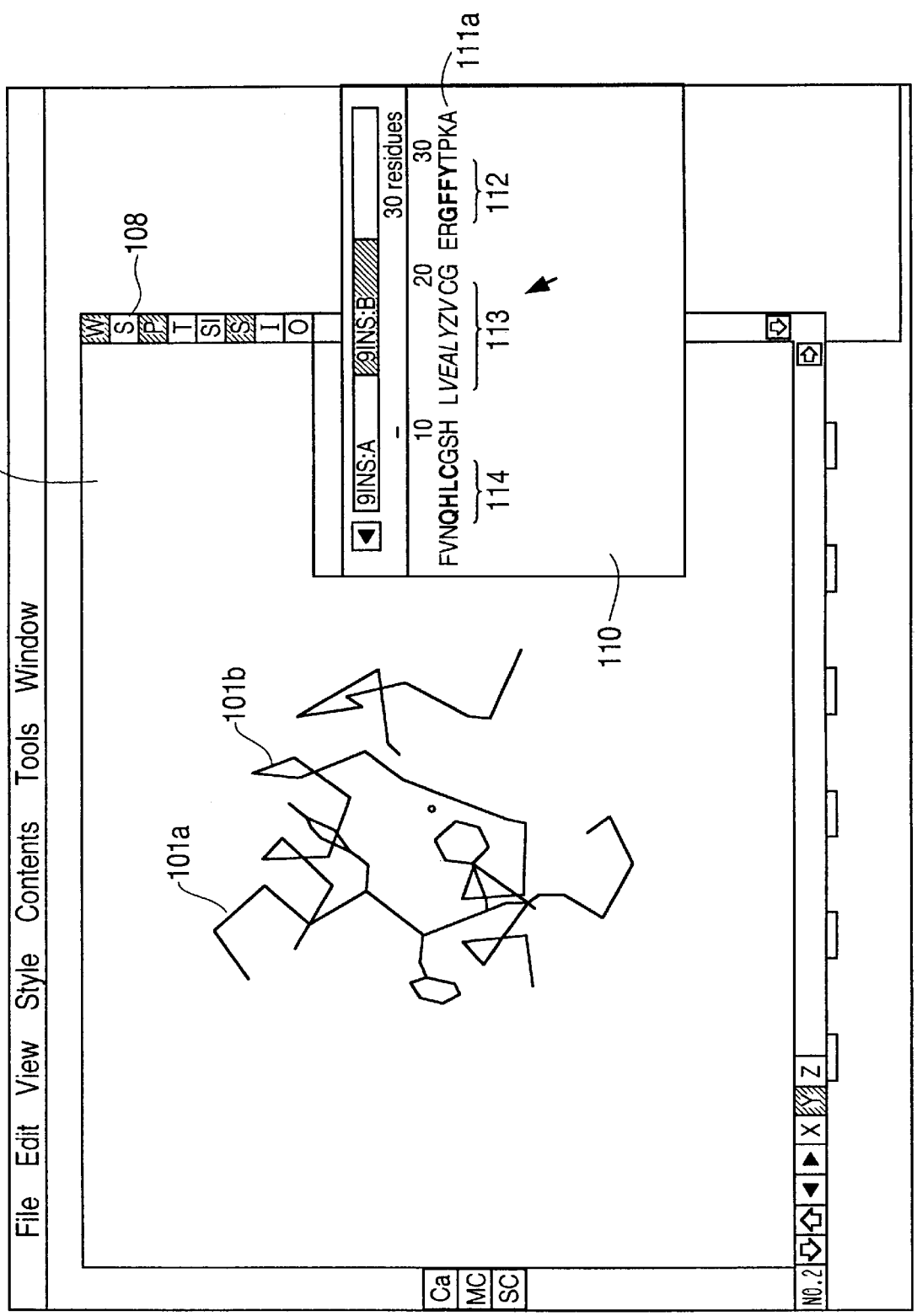
FIG. 11 is a schematic illustration showing another example of the display in the present invention.

In FIG. 11, a portion 114 in the character display 111a of the protein shown in the character display window 110 shown in FIG. 10 is designated, and the portion 114 is cut off by selecting a row 85a in the display mode changing menu.

In this case, a portion 114 is displayed as an outline font and the graphic display window 100 is not different from that shown in FIG. 10. However, when the button 108 in the display window is pressed to switch the display, a portion corresponding to the portion 114 is displayed in the whole graphic display window 100.

Figure 12:
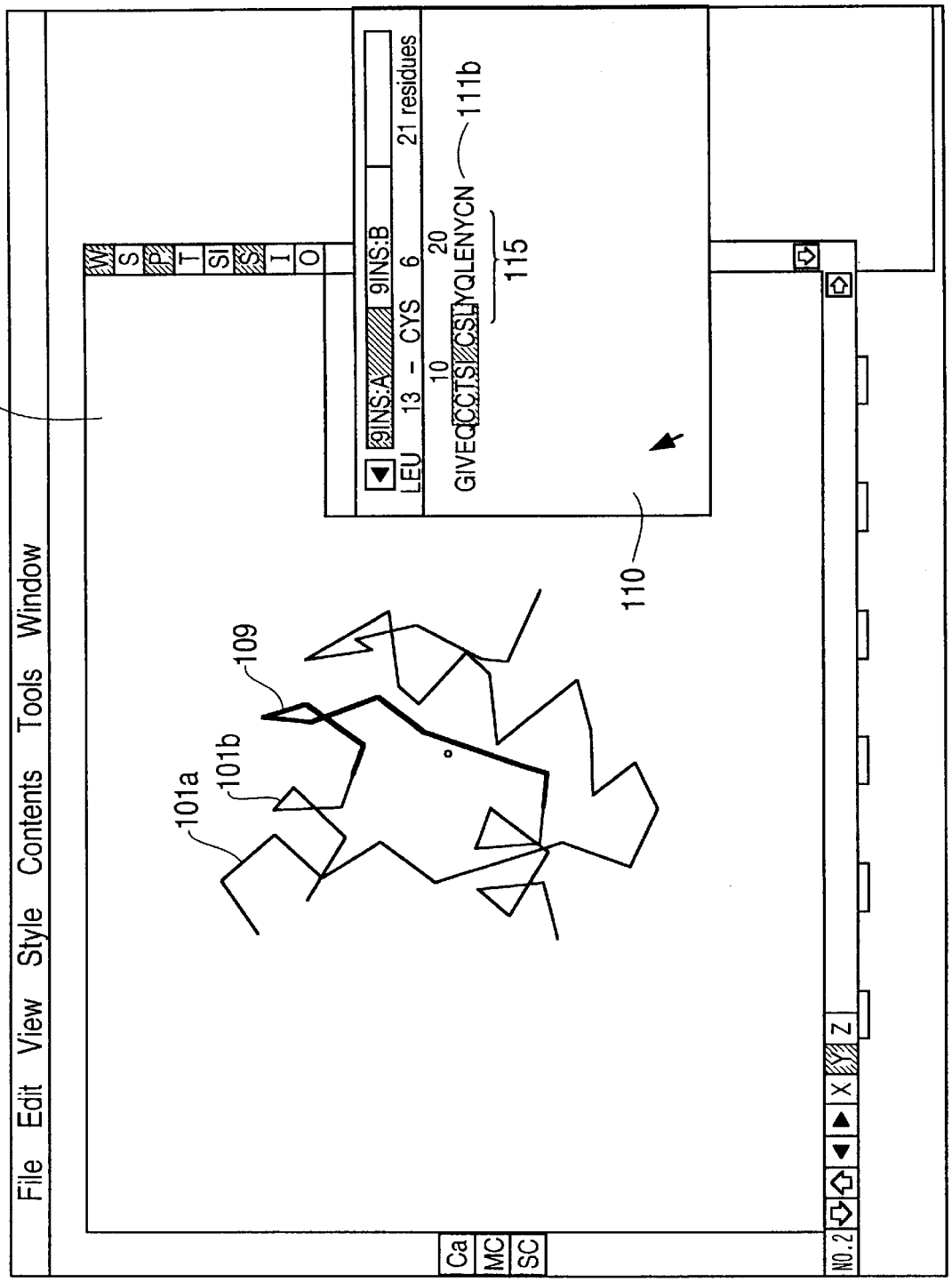
FIG. 12 is a schematic illustration showing another example of the display in the present invention.

In FIG. 12, a portion 109 of the graphic display 101b of the protein in the graphic display window 100 shown in FIG. 8 is designated and a line width in the portion 109 is made larger by selecting from columns 77, 78 in the display mode changing menu. According to the invention, the line in the portion 109 is made thicker.

In the character display 111b of the protein in the character display window 110, the portion 115 corresponding to the portion 109 is reversed in color using the bold face type.

In this device, the graphic display relates to the character display. Thus, the designation of the portion displayed and the setting of the display mode in either the graphic display or the character display can be reflected in the other display. That is, a specific portion can be seen in both the graphic display and the character display. Accordingly, a chemist unskilled with computers can operate the device easily.

When a specific portion in a first-order structure of a protein described in an article or a paper is designated in the character display, a stereo structure of that designated portion is displayed distinguished from the remaining part and can be visibly analyzed.

According to the invention, a nucleic acid or a hetero atomic compound can be displayed on a graphic display or a character display. In this context, examples of the nucleic acid include DNA and RNA. An example of the hetero atom is a material reactive with a protein and a nucleic acid, which includes an ionic molecule, a water molecule, a coenzyme, HEME (complex of iron and protoporphyrin) and a base.

Figure 13:
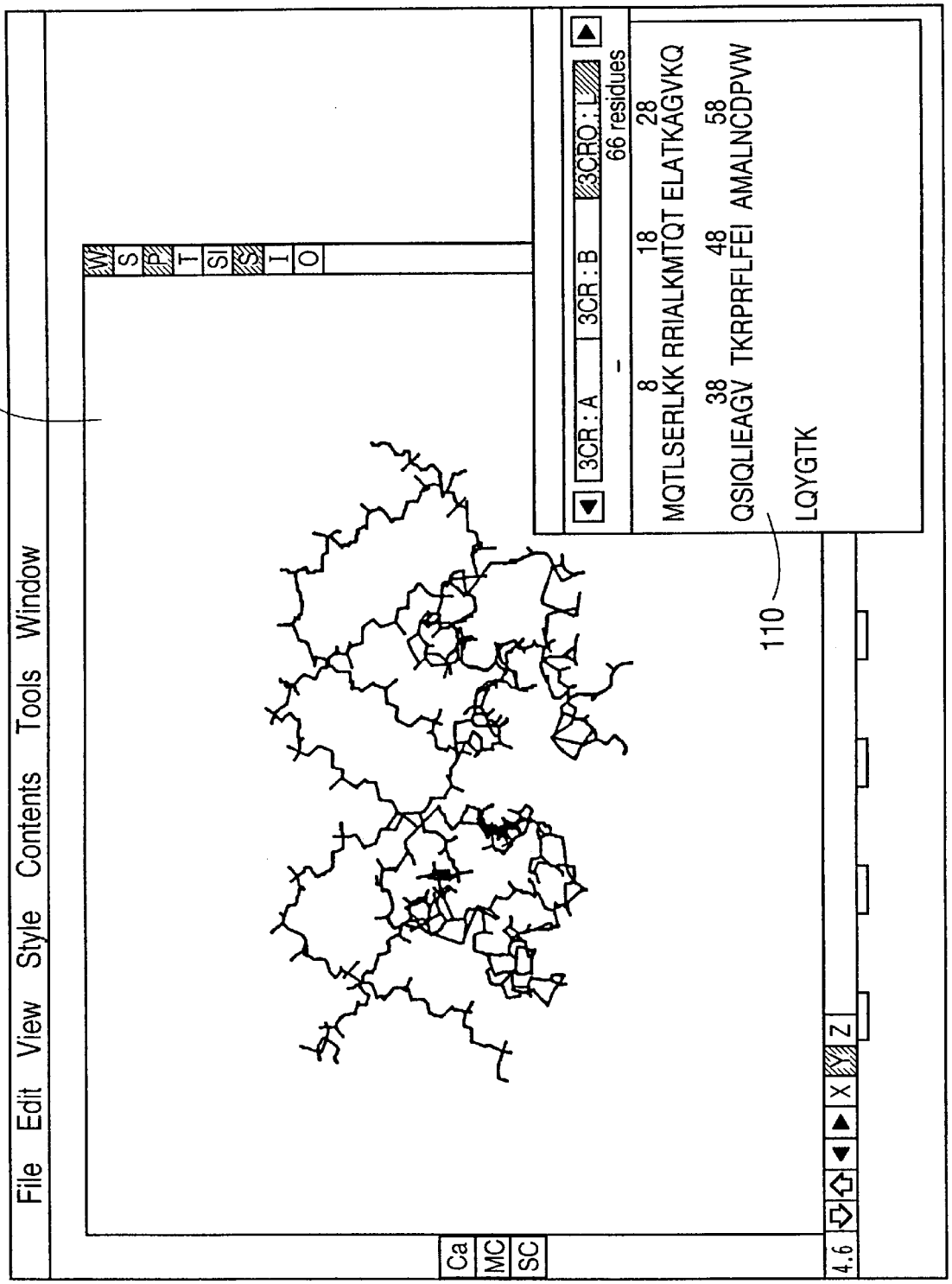
FIG. 13 is a schematic illustration showing another example of the display in the present invention.

In FIG. 13, a stereo structure of a nucleic acid is displayed in the graphic display window 100 and a character display of the nucleic acid is displayed in which the bases constituting the nucleic acids are represented by letters in the character display window 110. In this case, the display unit buffer 30 is formed for each nucleic acid unit.

Figure 14:
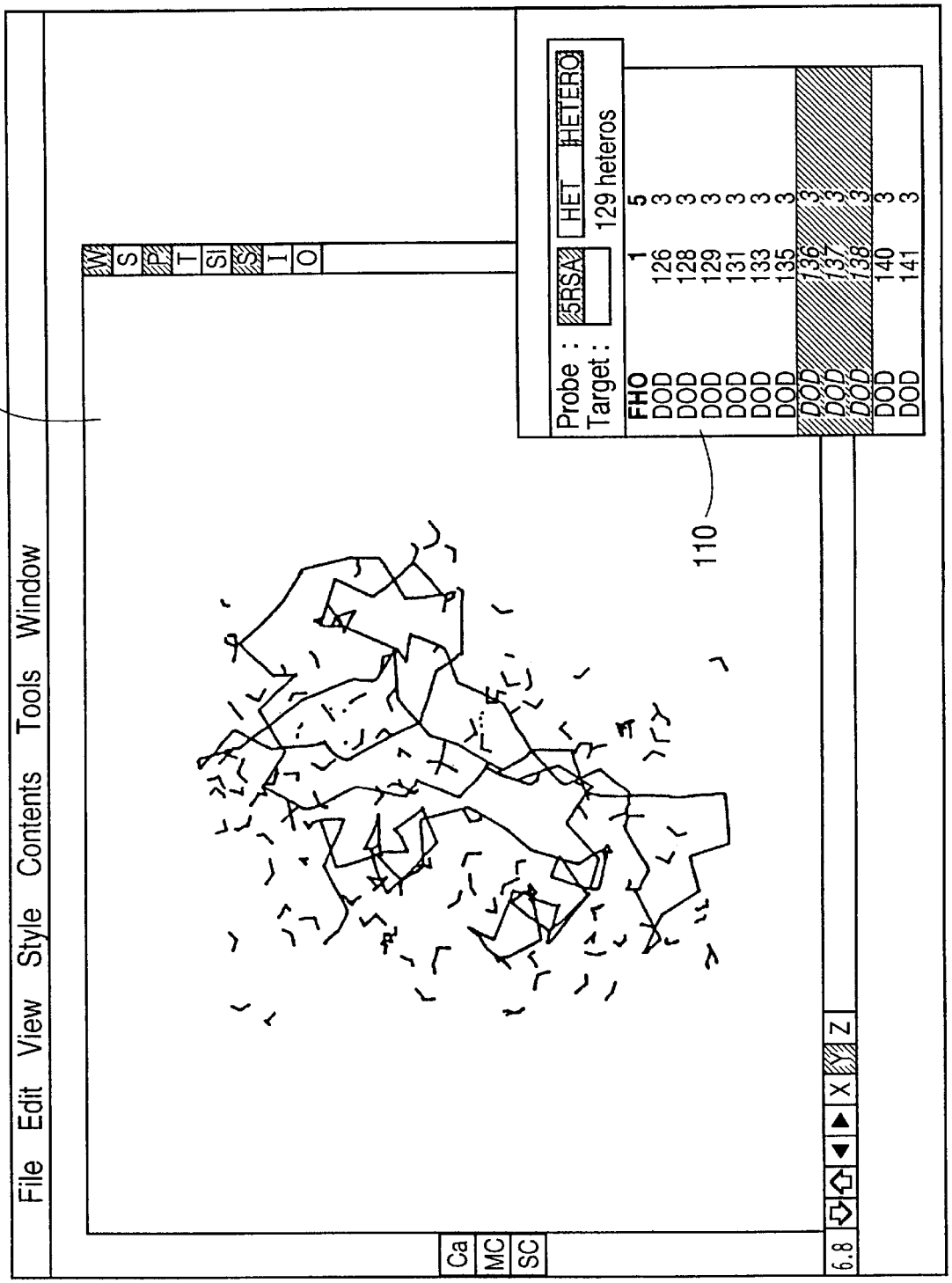
FIG. 14 is a schematic illustration showing another example of the display of the present invention.

In FIG. 14, a stereo structure of the hetero atom is displayed in the graphic display window 100, in which each hetero atom is represented by a character. In this case, the display unit buffer 30 is prepared for each hetero atom unit.

Further, the present invention is not limited to these embodiments, but various variations and modifications may be made without departing from the scope of the present invention.

What is claimed:

1. A method for displaying a structure of a compound with reference to a database in which stereo structural data of said compound is stored, comprising the steps of:

recording said stereo structural data obtained from said database in a display buffer having a designated area for setting a display mode;

displaying graphically in a first window a stereo structure of said compound based on said recorded stereo structural data, said structure displayed corresponding to said display mode set in said designated area; and simultaneously displaying in a second window characters representing said stereo structure of said compound corresponding to said display mode set in said designated area, wherein at least said second window serves as a user interface, and wherein said compound is a protein and said display buffer is a group of display unit buffers for each amino acid residue unit of said protein.

2. A method for displaying a structure of a compound with reference to a database in which stereo structural data of said compound is stored, comprising the steps of:

recording said stereo structural data obtained from said database in a display buffer having a designated area for setting a display mode;

displaying graphically in a first window a stereo structure of said compound based on said recorded stereo structural data, said structure displayed corresponding to said display mode set in said designated area; and simultaneously displaying in a second window characters representing said stereo structure of said compound corresponding to said display mode set in said designated area, wherein at least said second window serves as a user interface, and wherein said compound comprises a nucleic acid and said display buffer comprises a group of display unit buffers for each base unit of said nucleic acid.

3. A method for displaying a structure of a compound with reference to a database in which stereo structural data of said compound is stored, comprising the steps of:

recording said stereo structural data obtained from said database in a display buffer having a designated area for setting a display mode;

displaying graphically in a first window a stereo structure of said compound based on said recorded stereo structural data, said structure displayed corresponding to said display mode set in said designated area; and simultaneously displaying in a second window characters representing said stereo structure of said compound corresponding to said display mode set in said designated area, wherein at least said second window serves as a user interface, and wherein said compound comprises an hetero atomic compound and said display buffer comprises a group of display unit buffers for each hetero atom unit of said hetero atomic compound.

4. A device displaying a structure of a compound, comprising:

a database in which stereo structural data of said compound is stored;

a display buffer in which said stereo structural data of said database is recorded, said display buffer being provided with a designated area for setting a display mode; and a display simultaneously displaying, in a first window, a stereo structure of said compound, based on the stored stereo structural data of said compound and, in a second window, characters representing said stereo structure of said compound being displayed in said first window, corresponding to said display mode set in said designated area, wherein at least said second window serves as a user interface, and wherein said compound comprises a protein and said display buffer comprises a group of display unit buffers for each amino acid residue unit of said protein.

5. A device displaying a structure of a compound, comprising:

a database in which stereo structural data of said compound is stored;

a display buffer in which said stereo structural data of said database is recorded, said display buffer being provided with a designated area for setting a display mode; and a display simultaneously displaying, in a first window, a stereo structure of said compound, based on the stored stereo structural data of said compound and, in a second window, characters representing said stereo structure of said compound being displayed in said first window, corresponding to said display mode set in said designated area, wherein at least said second window serves as a user interface, and wherein said compound comprises a nucleic acid and said display buffer comprises a group of display unit buffers for each base unit of said nucleic acid.

6. A device displaying a structure of a compound, comprising:
a database in which stereo structural data of said compound is stored;
a display buffer in which said stereo structural data of said database is recorded, said display buffer being provided with a designated area for setting a display mode; and
a display simultaneously displaying, in a first window, a stereo structure of said compound, based on the stored stereo structural data of said compound and, in a second window, characters representing said stereo structure of said compound being displayed in said first window, corresponding to said display mode set in said designated area,
wherein at least said second window serves as a user interface, and
wherein said compound comprises a hetero atomic compound and said display buffer comprises a group of display unit buffers for each hetero atom unit of said hetero atomic compound.

7. A method for displaying a structure of a compound with reference to a database in which stereo structural data of said compound is stored, comprising the steps of:
recording said stereo structural data obtained from said database in a display buffer having a designated area for setting a display mode;
displaying graphically a stereo structure of said compound corresponding to said display mode set in said designated area; and
displaying characters representing said stereo structure of said compound corresponding to said display mode set in said designated area,
wherein said compound is a protein and said display buffer is a group of display unit buffers for each amino acid residue unit of said protein.

8. The method for displaying a structure of a compound according to claim 7, wherein said display mode is determined by setting at least one of a shape, a color, a line width and a line type defining said stereo structure of said compound, and at least one of a font, a highlight and a color of said characters representing said structure of said compound.

9. A method for displaying a structure of a compound with reference to a database in which stereo structural data of said compound is stored, comprising the steps of:
recording said stereo structural data obtained from said database in a display buffer having a designated area for setting a display mode;
displaying graphically a stereo structure of said compound corresponding to said display mode set in said designated area; and
displaying characters representing said stereo structure of said compound corresponding to said display mode set in said designated area,
wherein said compound comprises a nucleic acid and said display buffer comprises a group of display unit buffers for each base unit of said nucleic acid.

10. The method for displaying a structure of a compound according to claim 9, wherein said display mode is determined by setting at least one of a shape, a color, a line width and a line type defining said stereo structure of said compound and at least one of a font, a highlight and a color of said characters representing said structure of said compound.

11. A method for displaying a structure of a compound with reference to a database in which stereo structural data of said compound is stored, comprising the steps of:
recording said stereo structural data obtained from said database in a display buffer having a designated area for setting a display mode;
display graphically a stereo structure of said compound corresponding to said display mode set in said designated area; and
displaying characters representing said stereo structure of said compound corresponding to said display mode set in said designated area,
wherein said compound comprises an hetero atomic compound and said display buffer comprises a group of display unit buffers for each hetero atom unit of said hetero atomic compound.

12. The method for displaying a structure of a compound according to claim 11, wherein said display mode is determined by setting at least one of a shape, a color, a line width and a line type defining said stereo structure of said compound and at least one of a font, a highlight and a color of said characters representing said structure of said compound.

13. A device displaying a structure of a compound, comprising:
a database in which stereo structural data of said compound is stored;
a display buffer in which said stereo structural data of said database is recorded, said display buffer being provided with a designated area for setting a display mode; and
a display displaying said structure of said compound, including a stereographic structure of said compound and characters representing said structure of said compound being displayed on said display, corresponding to said display mode set in said designated area,
wherein said compound comprises a protein and said display buffer comprises a group of display unit buffers for each amino acid residue unit of said protein.

14. The device for displaying a structure of a compound according to claim 13, wherein said display mode is determined by setting at least one of a shape, a color, a line width and a line type defining said stereo structure of said compound and at least one of a font, a highlight and a color of said characters representing said structure of said compound.

15. A device displaying a structure of a compound, comprising:
a database in which stereo structural data of said compound is stored;
a display buffer in which said stereo structural data of said database is recorded, said display buffer being provided with a designated area for setting a display mode; and
a display displaying said structure of said compound, including a stereographic structure of said compound and characters representing said structure of said compound being displayed on said display, corresponding to said display mode set in said designated area,
wherein said compound comprises a nucleic acid and said display buffer comprises a group of display unit buffers for each base unit of said nucleic acid.

16. The device for displaying a structure of a compound according to claim 15, wherein said display mode is determined by setting at least one of a shape, a color, a line width and a line type defining said stereo structure of said compound and at least one of a font, a highlight and a color of said characters representing said structure of said compound.

17. A device displaying a structure of a compound, comprising:

a database in which stereo structural data of said compound is stored;

a display buffer in which said stereo structural data of said database is recorded, said display buffer being provided with a designated area for setting a display mode; and a display displaying said structure of said compound, including a stereographic structure of said compound and characters representing said structure of said compound being displayed on said display, corresponding to said display mode set in said designated area, wherein said compound comprises a hereto atomic compound and said display buffer comprises a group of display unit buffers for each hereto atom unit of said hereto atomic compound.

18. The device for displaying a structure of a compound according to claim 17, wherein said display mode is determined by setting at least one of a shape, a color, a line width and a line type defining said stereo structure of said compound and at least one of a font, a highlight and a color of said characters representing said structure of said compound.

* * * * *